US012447644B2

(12) United States Patent
Buffo et al.

(10) Patent No.: US 12,447,644 B2
(45) Date of Patent: Oct. 21, 2025

(54) OSTOMY BAG PREPARATION DEVICE

(71) Applicants: Nicholas Marsh Buffo, Lenexa, KS (US); Maya Rae Federle, Columbus, IN (US); Nikita Rao, Westfield, IN (US); Diya Deepak Sakhrani, O'Fallon, MO (US); Sathveka Sembian, Libertyville, IL (US)

(72) Inventors: Nicholas Marsh Buffo, Lenexa, KS (US); Maya Rae Federle, Columbus, IN (US); Nikita Rao, Westfield, IN (US); Diya Deepak Sakhrani, O'Fallon, MO (US); Sathveka Sembian, Libertyville, IL (US)

( * ) Notice: Subject to any disclaimer, the term of this patent is extended or adjusted under 35 U.S.C. 154(b) by 0 days.

(21) Appl. No.: 18/668,625

(22) Filed: May 20, 2024

(65) Prior Publication Data

US 2025/0196388 A1 Jun. 19, 2025

Related U.S. Application Data

(60) Provisional application No. 63/610,070, filed on Dec. 14, 2023.

(51) Int. Cl.
*B26F 1/38* (2006.01)
*A61F 5/445* (2006.01)
(Continued)

(52) U.S. Cl.
CPC ............ *B26F 1/3846* (2013.01); *A61F 5/445* (2013.01); *B26D 7/0006* (2013.01); *B26D 7/27* (2013.01)

(58) Field of Classification Search
CPC ...... B26F 1/3846; A61F 5/445; B26D 7/0006; B26D 7/27
See application file for complete search history.

(56) References Cited

U.S. PATENT DOCUMENTS 157,841 A * 12/1874 King .......................... B43L 9/04 33/27.09
441,975 A * 12/1890 Rapieff .................... G01C 3/18 33/279
(Continued)

FOREIGN PATENT DOCUMENTS

BE 1026418 A1 * 1/2020
CN 210161262 U 3/2020
(Continued)

OTHER PUBLICATIONS

CN_212948053 (Year: 2021).*
(Continued)

*Primary Examiner* — Jonathan G Riley
(74) *Attorney, Agent, or Firm* — Morrison & Foerster LLP

(57) ABSTRACT

Described herein are devices and methods of use thereof for preparing ostomy bags for attachment to a stoma. The device can include an elongated housing, a cutting tool including a blade, and a measurement guide for measuring the diameter of a stoma, each of the cutting tool and the measurement guide surrounding a given portion of the elongated housing. The device can include a handle that comprises a pinion operably coupled to each of the cutting tool and the measurement guide by racks, such that engaging the handle causes each of the cutting tool and the measurement guide to translate along the elongated housing. The device can include a cutting base that is coupled to the elongated housing such that the cutting base is insertable into an opening of an ostomy bag and receives the blade of the cutting tool when cutting an adhesive portion of the ostomy bag.

19 Claims, 9 Drawing Sheets

(51) Int. Cl.
*B26D 7/00* (2006.01)
*B26D 7/27* (2006.01)

(56) References Cited

U.S. PATENT DOCUMENTS

| | | | | |
|---|---|---|---|---|
| 1,169,245 | A * | 1/1916 | Finch | B43L 13/22 33/561.3 |
| 4,426,781 | A * | 1/1984 | Kufrin | B26F 1/3846 30/310 |
| 4,762,738 | A | 8/1988 | Keyes | |
| 4,865,594 | A | 9/1989 | Thomas | |
| 4,911,051 | A * | 3/1990 | Depetris | B23B 51/05 30/310 |
| 5,356,399 | A | 10/1994 | Takahashi | |
| 6,286,216 | B1 * | 9/2001 | Braun | B26F 1/3846 30/310 |
| 6,659,989 | B1 | 12/2003 | Otto | |
| 6,796,211 | B1 * | 9/2004 | Braunberger | B26F 1/3846 30/310 |
| 7,087,041 | B2 | 8/2006 | Von Dyck | |
| 7,381,715 | B2 | 6/2008 | Sabesan | |
| 7,424,780 | B2 * | 9/2008 | Cicchitti | B26F 1/3846 30/310 |
| 7,550,430 | B2 | 6/2009 | Keeler | |
| 7,685,719 | B2 * | 3/2010 | Hogan | B26F 1/3846 30/310 |
| 8,002,759 | B2 | 8/2011 | Andersen | |
| 8,043,632 | B2 | 10/2011 | Sabesan | |
| 8,092,815 | B2 | 1/2012 | Sabesan | |
| 9,044,340 | B2 | 6/2015 | Strbech | |
| 9,549,839 | B2 | 1/2017 | Schertiger | |
| 10,070,987 | B2 | 9/2018 | Scott | |
| 10,251,773 | B2 | 4/2019 | Schertiger | |
| 10,413,440 | B2 | 9/2019 | Moavenian | |
| 11,033,418 | B2 | 6/2021 | O'brien | |
| 11,160,681 | B2 | 11/2021 | Strøbech | |
| 11,278,640 | B2 | 3/2022 | Stroebech | |
| 2002/0077611 | A1 | 6/2002 | Von Dyck | |
| 2004/0171999 | A1 | 9/2004 | Andersen | |
| 2005/0065072 | A1 | 3/2005 | Keeler | |
| 2005/0118239 | A1 | 6/2005 | Sabesan | |
| 2005/0154361 | A1 | 7/2005 | Sabesan | |
| 2006/0177489 | A1 | 8/2006 | Massouda | |
| 2007/0255240 | A1 | 11/2007 | Ciok | |
| 2008/0193494 | A1 | 8/2008 | Sabesan | |
| 2013/0072886 | A1 | 3/2013 | Schertiger | |
| 2013/0138064 | A1 | 5/2013 | Stroebech | |
| 2014/0276500 | A1 | 9/2014 | Scott | |
| 2016/0235582 | A1 | 8/2016 | Moavenian | |
| 2017/0143533 | A1 | 5/2017 | Schertiger | |
| 2018/0116859 | A1 | 5/2018 | Strøbech | |
| 2018/0296384 | A1 | 10/2018 | O'brien | |
| 2019/0015243 | A1 | 1/2019 | Scott | |
| 2019/0134256 | A1 | 5/2019 | Stroebech | |
| 2022/0117771 | A1 | 4/2022 | Fearn | |
| 2022/0249271 | A1 | 8/2022 | Stroebech | |
| 2023/0081026 | A1 | 3/2023 | Mahood | |
| 2023/0137568 | A1 | 5/2023 | Peet | |

FOREIGN PATENT DOCUMENTS

| | | | |
|---|---|---|---|
| CN | 210500460 | U | 5/2020 |
| CN | 210850472 | U * | 6/2020 |
| CN | 212948053 | U * | 4/2021 |
| CN | 215358668 | U | 12/2021 |
| CN | 217098032 | U * | 8/2022 |
| CN | 221285726 | U * | 7/2024 |
| WO | 00/25709 | A1 | 5/2000 |
| WO | 2005/019241 | A2 | 3/2005 |
| WO | 2005/019315 | A1 | 3/2005 |
| WO | 2006/086339 | A2 | 8/2006 |
| WO | 2011/134482 | A2 | 11/2011 |
| WO | 2011/150936 | A1 | 12/2011 |
| WO | 2015/052092 | A1 | 4/2015 |
| WO | 2015/058114 | A1 | 4/2015 |
| WO | 2015/090332 | A1 | 6/2015 |
| WO | 2016/162038 | A1 | 10/2016 |
| WO | 2017/067557 | A2 | 4/2017 |
| WO | 2017/067558 | A1 | 4/2017 |
| WO | 2017/075320 | A1 | 5/2017 |
| WO | 2017/152921 | A1 | 9/2017 |
| WO | 2019/120453 | A1 | 6/2019 |
| WO | 2020/123771 | A2 | 6/2020 |
| WO | 2020/200382 | A1 | 10/2020 |
| WO | 2021/165705 | A1 | 8/2021 |
| WO | 2021/202314 | A1 | 10/2021 |
| WO | 2022/082215 | A1 | 4/2022 |

OTHER PUBLICATIONS

BE_1026418_A1 (Year: 2020).*
CN_210850472 (Year: 2020).*
CN_221285726.*
CN_217098032_U (Year: 2022).*

* cited by examiner

OSTOMY BAG PREPARATION DEVICE

CROSS-REFERENCE TO RELATED APPLICATIONS

This application claims the benefit of and priority to U.S. Provisional Patent Application No. 63/610,070, filed Dec. 14, 2023, the contents of which are incorporated herein by reference in its entirety.

FIELD OF THE DISCLOSURE

The present disclosure relates generally to the field of medical devices and methods, and more specifically to devices for preparing ostomy bags for use.

BACKGROUND

In the United States, over one million individuals currently live with an ostomy due to the removal of diseased bowel. Up to 75% of these patients experience peristomal skin irritation due to leakage of stoma output onto the peristomal skin from ill-fitting ostomy bags. Currently, patients measure and cut their bags approximately every three days using a paper measuring guide and curved scissors. However, this multi-step system is time-consuming and does not provide precise sizing. Accordingly, there exists a need for a solution to efficiently measure the stoma and cut an appropriately-sized hole in ostomy bags with one integrated device.

SUMMARY

Disclosed herein are ostomy bag preparation devices and methods of use thereof for measuring a stoma and cutting a corresponding-sized hole in an ostomy bag. The device can include a bilateral measurement system that enables a user to measure the diameter of a stoma on a continuous measurement scale. The measurement system can be composed of a measurement guide and a cutting tool slidably attached to an elongated housing. Each of the measurement guide and the cutting tool can be coupled to a handle via a linear actuator for equidistantly translating the cutting tool and measurement guide along the elongated housing. The cutting tool can include a blade shield that removably shields a blade for cutting the ostomy bag. The device can include a cutting base insertable to the existing opening in the ostomy bag prior to cutting and configured to receive the blade when cutting the ostomy bag to protect the back layer of the ostomy bag. Once the cutting tool is aligned with the desired ostomy bag diameter, the ostomy bag preparation device can be rotated to cut along the circumference of the desired hole size, in turn increasing cutting efficiency and accuracy of ostomy bags.

In some examples, a device for preparation of an ostomy bag system is provided, comprising: an elongated housing; a cutting tool comprising a blade, the cutting tool at least partially surrounding a first portion of the elongated housing; a measurement guide configured to measure a diameter of a stoma of a subject, the measurement guide at least partially surrounding a second portion of the elongated housing; a handle comprising a pinion inserted to an opening of the elongated housing, the handle operably coupled to the cutting tool by a first rack and to the measurement guide by a second rack, the first rack and the second rack disposed within the elongated housing, and wherein engaging the handle causes each of the cutting tool and the measurement guide to translate along the elongated housing; and a cutting base coupled to the elongated housing at an end of the cutting base, the cutting base insertable to an opening of an ostomy bag and configured to receive the blade of the cutting tool during cutting of an adhesive portion of the ostomy bag.

In some examples, the device comprises a blade shield configured to removably cover at least the blade of the cutting tool. In some examples, at least one of the cutting tool and the blade shield comprise a marker to indicate the diameter of the stoma and a corresponding cutting diameter for the ostomy bag. In some examples, the measurement guide comprises a marker to indicate the diameter of the stoma and the corresponding cutting diameter for the ostomy bag. In some examples, the elongated housing comprises measurement markings to measure the diameter of the stoma. In some examples, engaging the handle causes (a) the measurement guide to translate along the elongated housing in a first direction, and (b) the cutting tool to translate along the elongated housing in a second direction, the second direction opposite the first direction. In some examples, the measurement guide and the cutting tool are configured to translate along the elongated housing equidistantly. In some examples, the handle comprises a knob, such that engaging the handle comprises rotating the knob to cause the measurement guide and the cutting tool to translate along the elongated housing. In some examples, the blade of the cutting tool extends outward from a ring portion of the cutting tool toward the cutting base coupled to the elongated housing. In some examples, the elongated housing comprises at least one track extending at least a portion of a length of the elongated housing, the at least one track configured to guide translation of the cutting tool and the measurement guide along the elongated housing. In some examples, the elongated housing comprises a hinge that couples the end of the cutting base to the elongated housing, the cutting base configured to pivot about the hinge of the elongated housing. In some examples, the elongated housing comprises: a first housing portion; a second housing portion; and a connector surrounding at least a portion of each of the first housing portion and the second housing portion to connect the first housing portion and the second housing portion, wherein the first housing portion and the second housing portion enclose the first rack, the second rack, and the pinion of the handle. In some examples, a length of the elongated housing is between 50-150 mm. In some examples, a length of the cutting base is at least 50% of the length of the elongated housing.

In some examples, a method for preparing an ostomy bag system is provided, comprising: aligning an elongated housing of a device with a diameter of a stoma of a subject, the device comprising: a cutting tool comprising a blade, the cutting tool at least partially surrounding a first portion of the elongated housing; a measurement guide at least partially surrounding a second portion of the elongated housing; a handle comprising a pinion inserted to an opening of the elongated housing, the handle operably coupled to the cutting tool by a first rack and to the measurement guide by a second rack, the first rack and the second rack disposed within the elongated housing; and a cutting base coupled to the elongated housing at an end of the cutting base; engaging the handle to cause the cutting tool and the measurement guide to translate along the elongated housing such that each of the measurement guide and the cutting tool align with the diameter of the stoma; inserting the cutting base into an opening of an ostomy bag; and rotating the elongated housing to cut through an adhesive portion of the ostomy bag using the blade of the cutting tool.

In some examples, the device comprises a blade shield removably covering at least the blade of the cutting tool, and the method comprises removing the blade shield after engaging the handle to measure the stoma and before rotating the elongated housing to cut the adhesive portion of the ostomy bag. In some examples, engaging the handle causes (a) the measurement guide to translate along the elongated housing in a first direction, and (b) the cutting tool to translate along the elongated housing in a second direction, the second direction opposite the first direction. In some examples, the measurement guide and the cutting tool translate along the elongated housing equidistantly. In some examples, the handle comprises a knob, such that engaging the handle comprises rotating the knob to cause the measurement guide and the cutting tool to translate along the elongated housing. In some examples, the elongated housing comprises a hinge that couples the end of the cutting base to the elongated housing, such that inserting the cutting base into the opening of the stoma bag comprises pivoting the cutting base about the hinge of the elongated housing.

DESCRIPTION OF THE FIGURES

The present application can be best understood by reference to the following description taken in conjunction with the accompanying figures included in the specification.

DETAILED DESCRIPTION

Figure 1A:
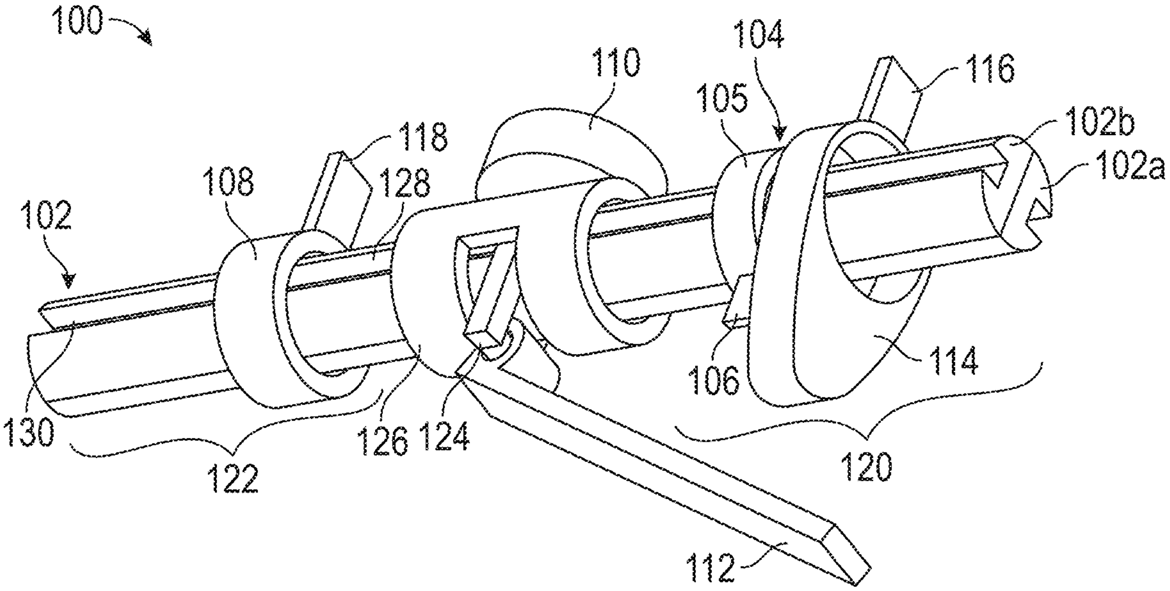
FIG. 1A illustrates a perspective view of an exemplary ostomy bag preparation device, in accordance with some embodiments.
Figure 1B:
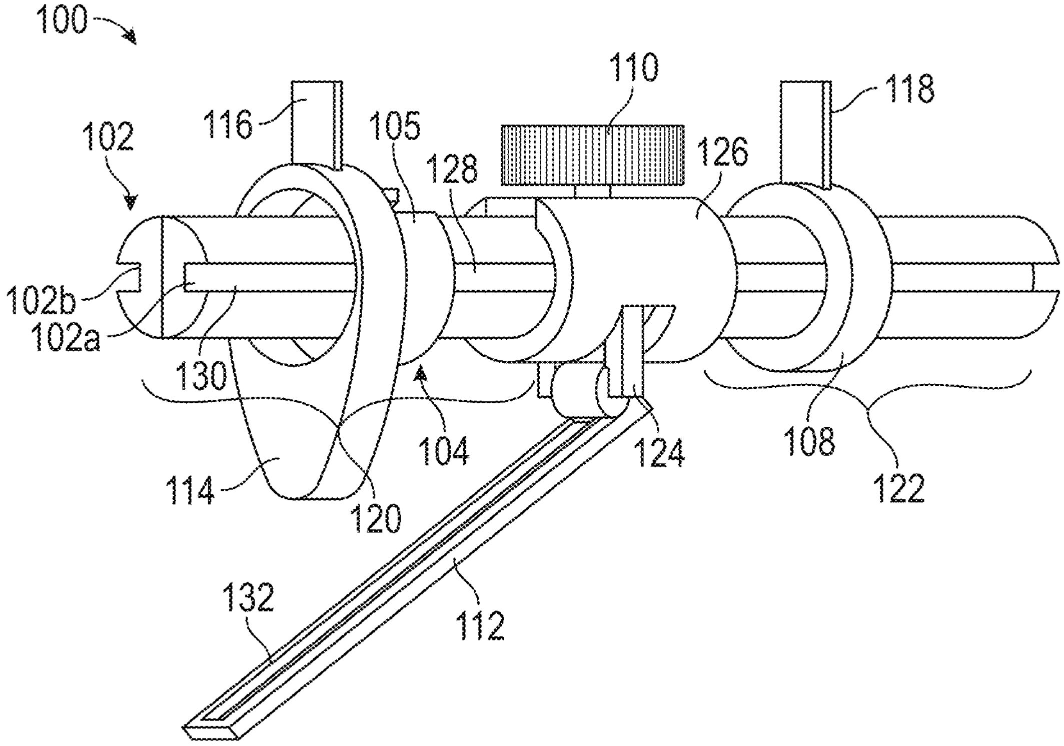
FIG. 1B illustrates another perspective view of the exemplary ostomy bag preparation device, in accordance with some embodiments.
Figure 1C:
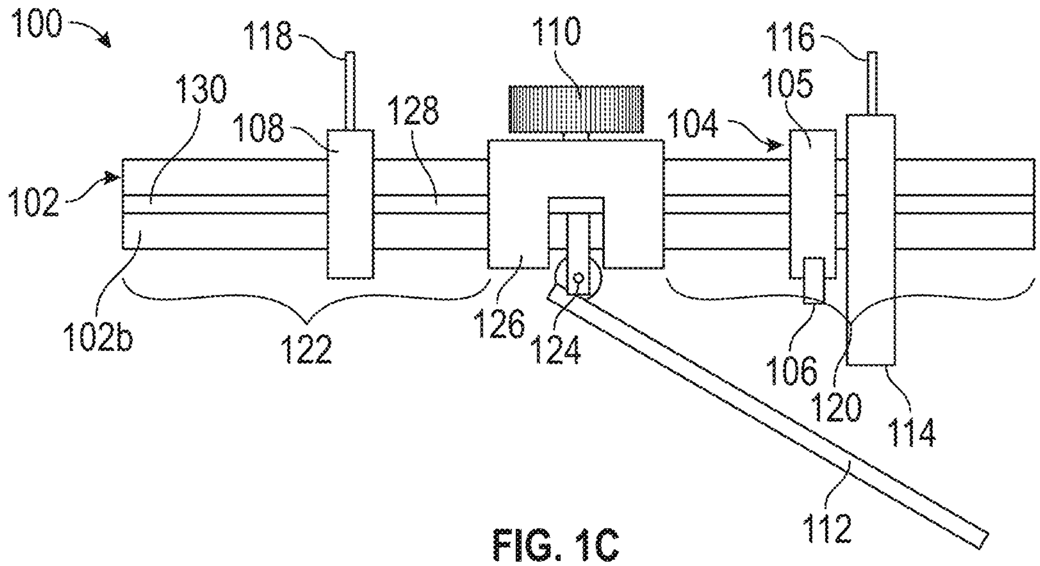
FIG. 1C illustrates a side view of the exemplary ostomy bag preparation device, in accordance with some embodiments.
Figure 1D:
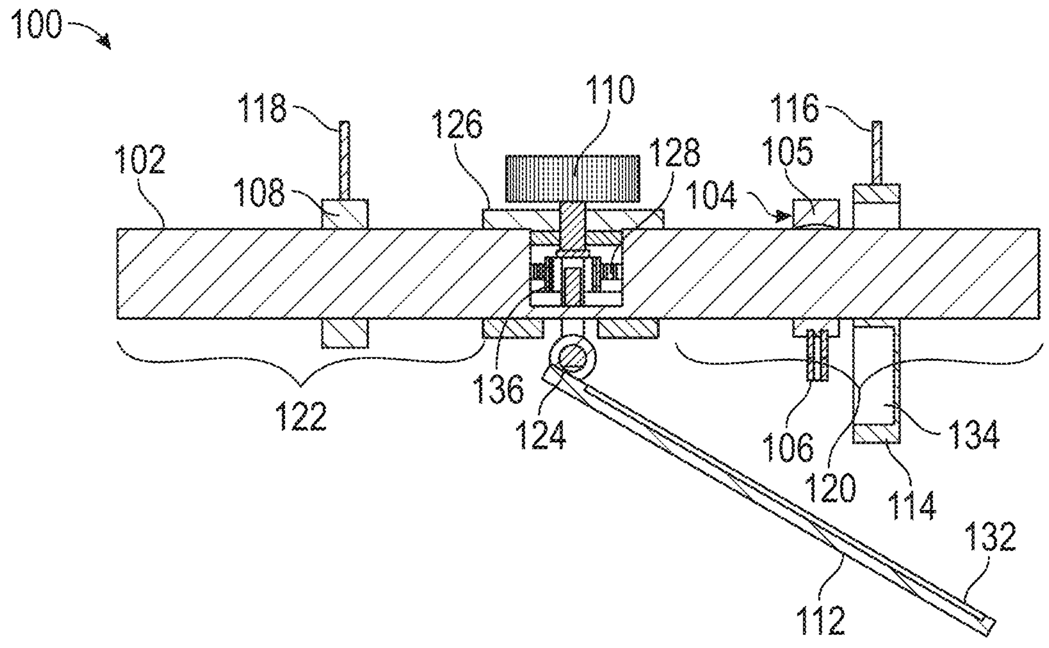
FIG. 1D illustrates a longitudinal cross-sectional view of the exemplary ostomy bag preparation device, in accordance some embodiments.

Provided herein are devices and methods of use thereof for both measuring a stoma and cutting a corresponding-sized hole in an ostomy bag. The device described herein can include a bilateral equal measurement system that enables a user to measure the diameter of the stoma on a continuous measurement scale from about 15 to 100 mm in diameter. The device can include an elongated housing with a cutting tool and measurement guide slidably attached thereto. The device can include a cutting base coupled to the elongated housing for insertion into the existing opening in the ostomy bag prior to cutting. The device can include a handle coupled to each of the cutting tool and the measurement guide for translating the cutting tool and the measurement guide along the elongated housing. The handle may be configured to increase accessibility of the device for users with dexterity limitations. Within the elongated housing, the device can include a linear actuator, such as a rack and pinion mechanism, that enables translation of the measurement guide and the cutting tool, each of which are coupled to a pinion of the handle by a rack. The cutting tool can move along the elongated housing and includes a blade attached thereto for cutting the ostomy bag.

The device can include a blade shield removably attached to the blade of the cutting tool. The one-sided blade and cutting base can enable the device to function properly with both one-piece and two-piece ostomy bag systems. The blade shield can include a measurement marker in addition to a blade shielding portion that houses the blade to ensure user safety when the device is not in use. The measurement guide can include a measurement marker for the portion of the elongated housing opposite the cutting tool, thereby enabling the user to cut based on the diameter rather than the radius of their stoma. The elongated housing itself can include measurement markers (e.g., a measurement ruler) for stoma diameter readout. The continuous measurement system both displayed along the elongated housing and further visualized using measurement markers can provide more precise measurements in comparison at least to the discrete sizing options on current paper measurement guides. Overall, the devices and methods provided herein can increase cutting efficiency and accuracy of ostomy bags, thereby mitigating stoma leakage and resulting skin irritation.

Various features of an exemplary ostomy bag preparation device will be described herein with reference to FIGS. 1A-1J. Following the description of the device, an exemplary method of use thereof for measuring a stoma and cutting an ostomy bag will be described herein with reference to FIGS. 2A-2F.

Ostomy Bag Preparation Devices

FIGS. 1A-1J illustrate various views of an exemplary ostomy bag preparation device 100. The device 100 can include an elongated housing 102, a cutting tool 104 that includes a blade 106, and a measurement guide 108 configured to measure a diameter of a stoma of a subject. The cutting tool 104 can at least partially surround the first portion 120 of the elongated housing 102. The measurement guide 108 can at least partially surround the second portion 122 of the elongated housing 102.

The device 100 can include a handle 110 operably coupled to the cutting tool 104 and the measurement guide 108 to translate each of the cutting tool 104 and the measurement guide 108. In some examples, the handle 110 can be a knob rotatable to cause the measurement guide 108 and the cutting tool 104 to translate along the elongated housing 102. In another example, the handle 110 may be a lever slidable to translate the cutting tool 104 and measurement guide 108 along the elongated housing 102. In some examples, the measurement guide 108 and the cutting tool 104 may translate along the elongated housing 102 equidistantly. In some examples, the elongated housing 102 can include one or more tracks 130 for guiding translation of the cutting tool 104 and/or the measurement guide 108 along the elongated housing 102, the one or more tracks 130 depicted in at least FIGS. 1A-1C. The one or more tracks 130 can include one or more grooves on one or more sides of the elongated housing 102. The one or more tracks 130 can extend at least a portion of a length of the elongated housing 102. For example, the elongated housing 102 may be between about 50-150 mm in length, and the one or more tracks may extend at least about 50%, 75%, 90%, 95%, or substantially all of the length of the elongated housing 102.

The handle 110 can be operably coupled to the cutting tool 104 and the measurement guide 108 via a linear actuator, such as a rack and pinion mechanism (e.g., pinion 136, racks 128). The pinion 136 can include teeth that are fitted with the teeth of the racks 128 at least partially disposed within the elongated housing 102 on either side of the pinion 136. The pinion 136 can be attached to or of the handle 110. One of the racks 128 (e.g., rack **128*a*) can be operably coupled to the cutting tool 104, and the other rack (e.g., rack 128*b*) can be operably coupled to the measurement guide 108. Thus, engaging (e.g., turning) the handle 110 can result in rotation of the pinion 136 and movement of the racks 128, which in turn causes movement of the measurement guide 108 and the cutting tool 104. Accordingly, turning the handle 110 can enable the user to easily move the measurement guide 108 and the cutting tool 104 to size their stoma. In some examples, engaging the handle can cause the measurement guide 108 to translate along the elongated housing 102 in a first direction, and the cutting tool 104 to translate along the elongated housing 102** in a second direction. The first direction can be opposite from the second direction.

The linear actuator can be at least partially enclosed within the elongated housing 102 because the elongated housing 102 can be composed from a first housing portion **102*a* and a second housing portion 102*b* that attach (e.g., removably attach). The first housing portion 102*a* and the second housing portion 102*b* can be attached by a connector 126 that surrounds at least a portion of the first housing portion 102*a* and the second housing portion 102*b*. The connector 126 can be disposed along the middle portion of the elongated housing 102, e.g., aligned with the handle 110, thereby applying pressure to the elongated housing 102 and ensuring contact between the teeth of the racks 128 and pinion 136**.

The blade 106 of the cutting tool 104 can extend outward from a ring portion 105 of the cutting tool 104 toward a cutting base 112 of the device 100. In some examples, the blade extends between about 5-15 mm from the ring portion 105 of the cutting tool 104, such as between about 5-12 mm, 5-10 mm, 8-15 mm, or 8-12 mm. The cutting base 112 can be configured to receive the blade 106 of the cutting tool 104 when cutting an adhesive portion of the ostomy bag, thereby protecting the back layer of one-piece ostomy bags. For example, the cutting base 112 can include a channel 132 configured to receive the blade 106, the channel 132 illustrated in at least FIG. 1D. The cutting base 112 of the device 100 can be coupled to the elongated housing 102 via a hinge 124 configured to receive an end of the cutting base 112. In this manner, the cutting base 112 can pivot about the hinge 124 to insert the cutting base 112 into an opening of an ostomy bag. The cutting base 112 can be sized such that it is insertable to the opening of the ostomy bag. For example, a length of the cutting base 112 may be at least about 50% of the length of the elongated housing 102. In some examples, the length of the cutting base 112 may be between about 25 mm and 75 mm.

In some examples, the device 100 includes a blade shield 114 configured to removably cover at least the blade 106 of the cutting tool 104 to ensure user safety when the device 100 is not in use. For example, the blade shield 114 can include a recess 134 configured to receive and shield the blade 106, the recess 134 depicted in at least FIG. 1D. The blade shield 114 can be removably attached to the cutting tool 104 so that during measurement of the stoma, the blade 106 is shielded, and after measurement and prior to cutting, the blade shield 114 can be removed to use the blade 106 for cutting the ostomy bag.

In some examples, at least one of the cutting tool 104 and the blade shield 114 include a marker configured to indicate the diameter of the stoma and a corresponding cutting diameter for the ostomy bag. The blade shield 114 of the device 100 includes a marker 116 that protrudes from a surface of the blade shield 114. In some examples, in addition to or instead of the cutting tool 104 and/or the blade shield 114 including a marker, the measurement guide 108 can include a marker for indicating the diameter of the stoma and the corresponding cutting diameter for the ostomy bag, thereby enabling the user to cut based on the diameter rather than the radius of the stoma. The marker 118 can protrude from a surface of the measurement guide 108. The marker 116 and/or 118 may be a tab that protrudes between about 5-15 mm from the surface of the blade shield 114 and measurement guide 108 (respectively). For example, the marker 116 and/or 118 may protrude between about 5-12 mm, 5-10 mm, 7-12 mm, or 7-10 mm from the surface of the blade shield 114 and measurement guide 108, respectively.

Figure 1E:
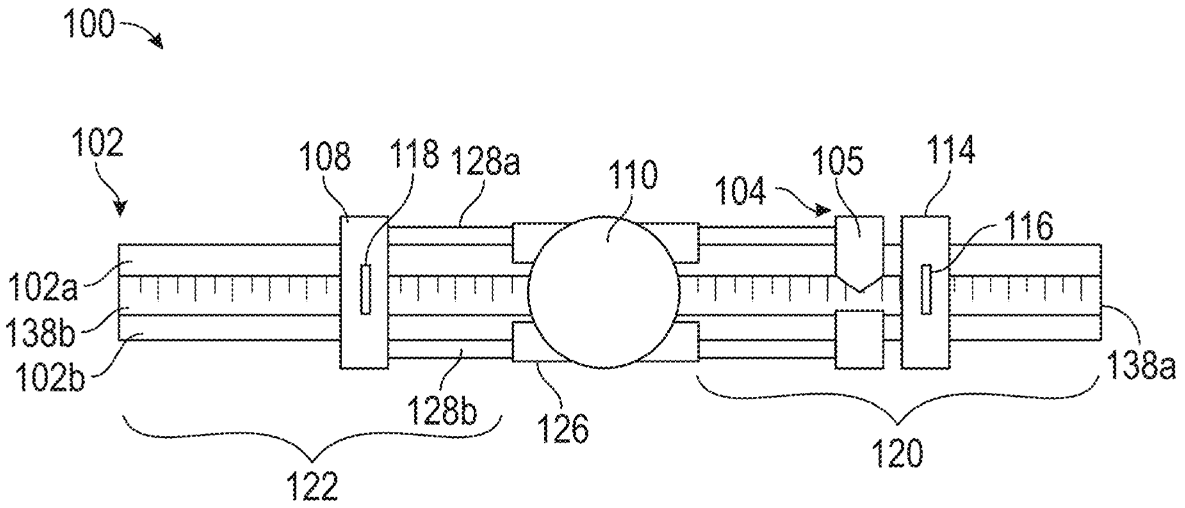
FIG. 1E illustrates a top view of the exemplary ostomy bag preparation device, in accordance with some embodiments.
Figure 1F:
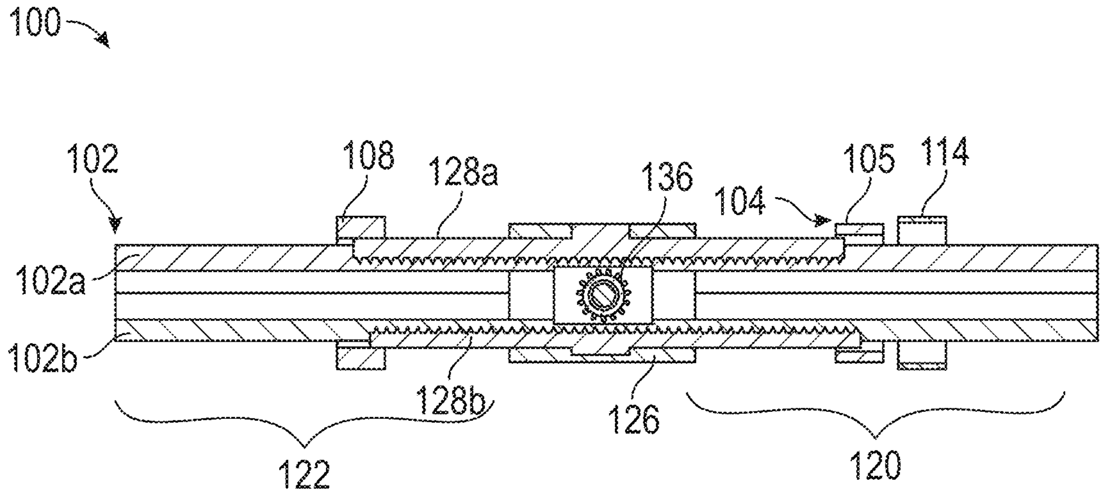
FIG. 1F illustrates a cross-sectional top view of the exemplary ostomy bag preparation device, in accordance with some embodiments.
Figure 1G:
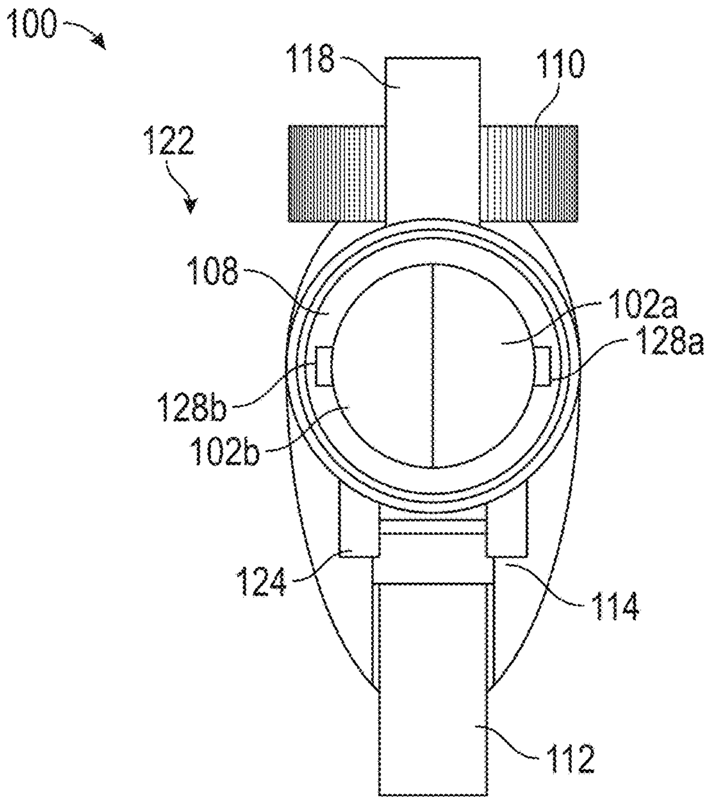
FIG. 1G illustrates a front view of the exemplary ostomy bag preparation device, in accordance with some embodiments.
Figure 1H:
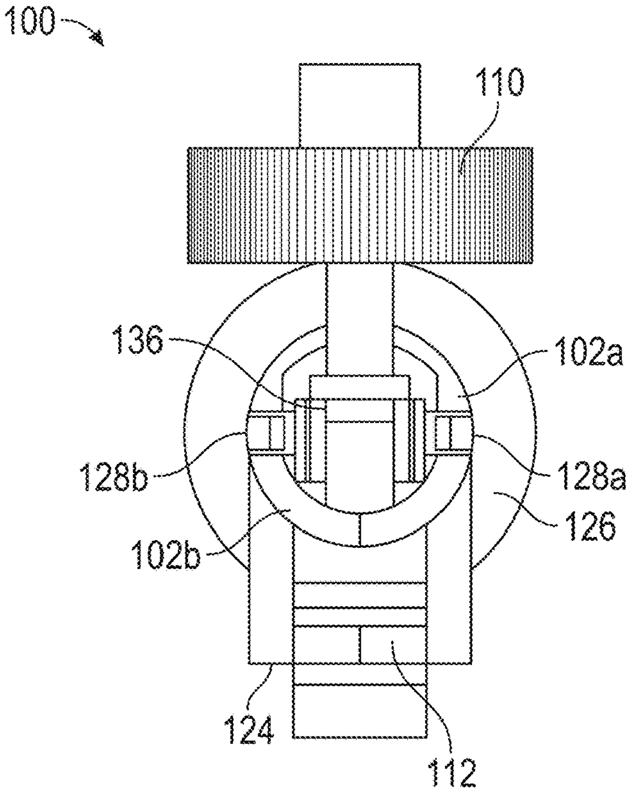
FIG. 1H illustrates a transverse cross-sectional view of the exemplary ostomy bag preparation device through the handle of the device, in accordance with some embodiments.
Figure 1I:
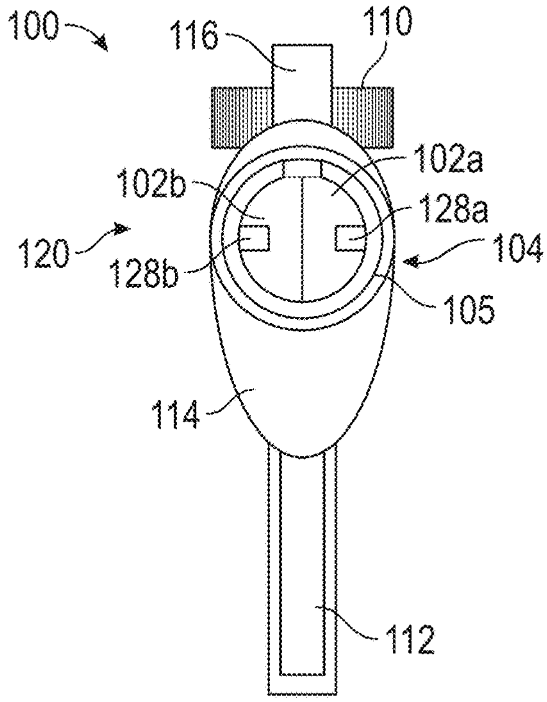
FIG. 1I illustrates a back view of the exemplary ostomy bag preparation device, in accordance with some embodiments.
Figure 1J:
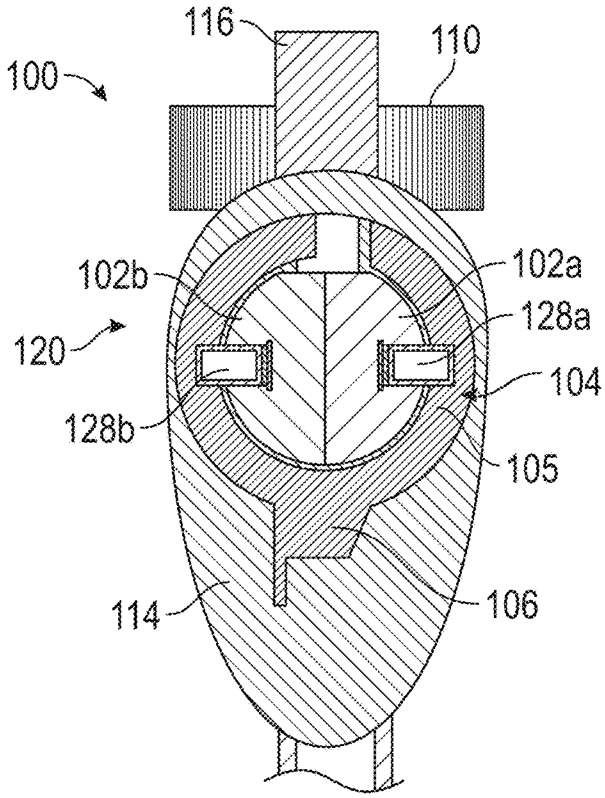
FIG. 1J illustrates a transverse cross-sectional view of the exemplary ostomy bag preparation device through the cutting blade shield, in accordance with some embodiments.

In some examples, the elongated housing 102 can include measurement markings for measuring the diameter of the stoma. FIG. 1E illustrates measurement markings **138*a* on the first portion 120 of the elongated housing 102, and measurement markings 138*b* on the second portion 122 of the elongated housing 102. The measurement markings 138*a*, 138*b*** may enable the user to measure stoma diameters between at least about 15 mm and 100 mm.

The elongated housing 102 can have a cylindrical, rectangular, or other polygonal shape, and the measurement guide 108 and the cutting tool 104 may be sized and shaped such that they can be slidably attached thereto. For example, the cutting tool 104 and/or the measurement guide 108 can include an annular (e.g., ring-shaped) or semi-annular ring that at least partially surrounds a cylindrically-shaped elongated housing 102. A width (e.g., diameter) of the elongated housing 102 may be between about 5-15 mm, such as between about 5-12 mm, 8-15 mm, or 8-12 mm. The inner width (e.g., diameter) of each of the cutting tool 104 and the measurement guide 108 about the same, e.g., between about 5-15 mm, such as between about 5-12 mm, 8-15 mm, or 8-12 mm. In some examples, the inner width of the diameter of the cutting tool 104 and the measurement guide 108 may be between about 0.1-2 mm greater than the width of the elongated housing 102, such as between about 0.1-1.5 mm, 0.1-1 mm, 0.5-1.5 mm, or 0.5-1 mm.

Methods for Preparing Ostomy Bags

Figure 2A:
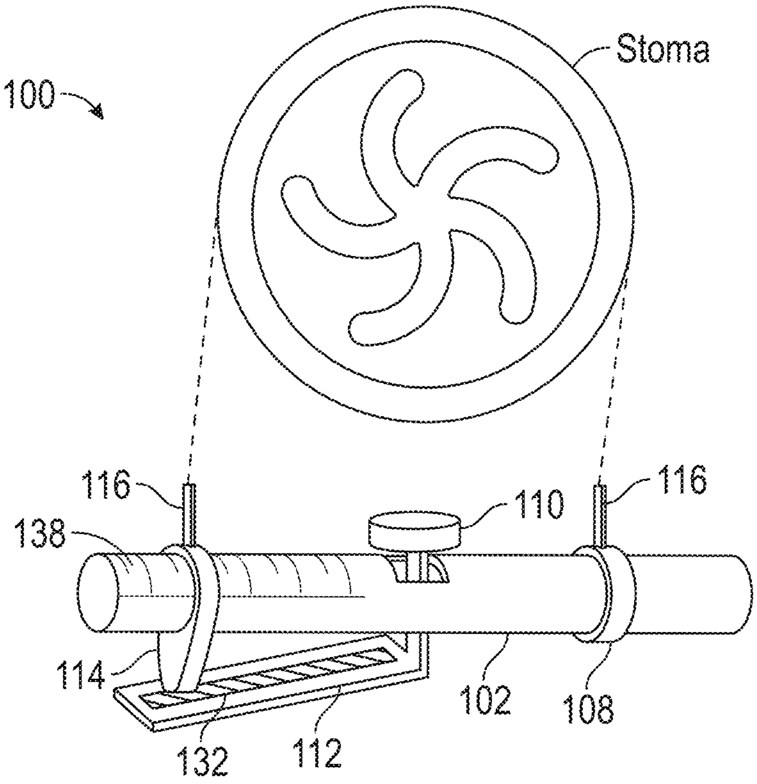
FIG. 2A illustrates aligning the elongated housing of an exemplary ostomy bag preparation device with the diameter of a stoma of a subject, in accordance with some embodiments.

FIGS. 2A-2F illustrate an exemplary method for preparing an ostomy bag using the device 100 described above. As shown in FIG. 2A, the method can include aligning the elongated housing 102 of the device 100 with a diameter of a stoma of a subject. Although the cutting tool 104 and the measurement guide 108 are depicted in alignment with the diameter of the stoma in FIG. 2A, it is to be understood that, because the cutting tool 104 and the measurement guide 108 are slidable relative to the elongated housing 102 of the device 100, this arrangement may not always initially occur.

Figure 2B:
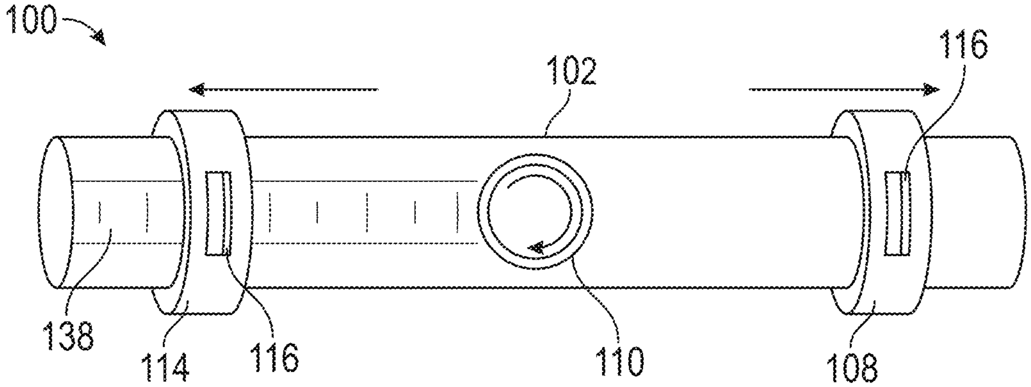
FIG. 2B illustrates engaging the handle of the exemplary ostomy bag preparation device to cause the cutting tool and the measurement guide to translate along the elongated housing such that each of the measurement guide and the cutting tool align with the diameter of the stoma, in accordance with some embodiments.

Accordingly, as shown in FIG. 2B, the method can include engaging the handle 110 to cause the cutting tool 104 and the measurement guide 108 to translate and align with the diameter of the stoma. As described above, the handle 110 can include a knob, such that engaging the handle 110 includes rotating the handle 110 to cause translation of the cutting tool 104 and the measurement guide 108. Engaging the handle 110 can cause the measurement guide 108 to translate along the elongated housing 102 in a first direction, and the cutting tool 104 to translate along the elongated housing in a second direction that is opposite the first direction. The measurement guide 108 and the cutting tool 104 can translate along the elongated housing 102 equidistantly.

Figure 2C:
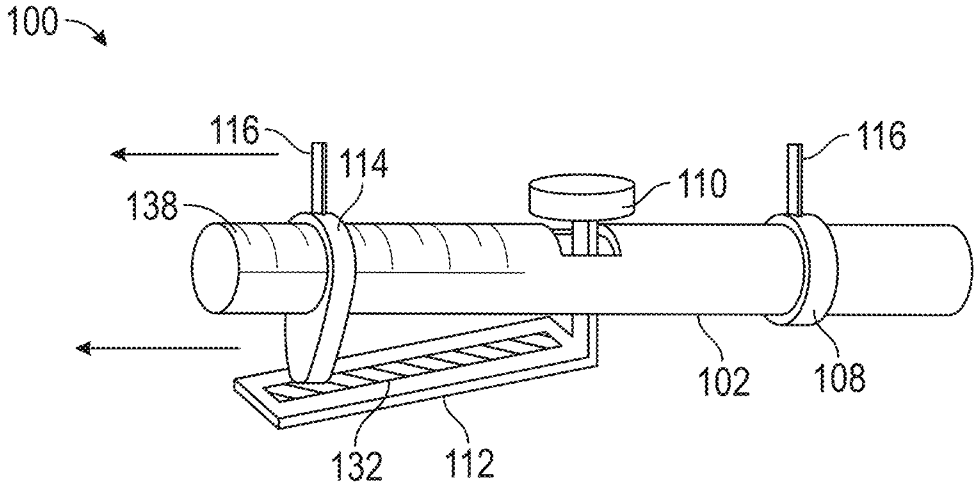
FIG. 2C illustrates removing the blade shield of the exemplary ostomy bag preparation device from covering at least the blade of the cutting tool, in accordance with some embodiments.
Figure 2D:
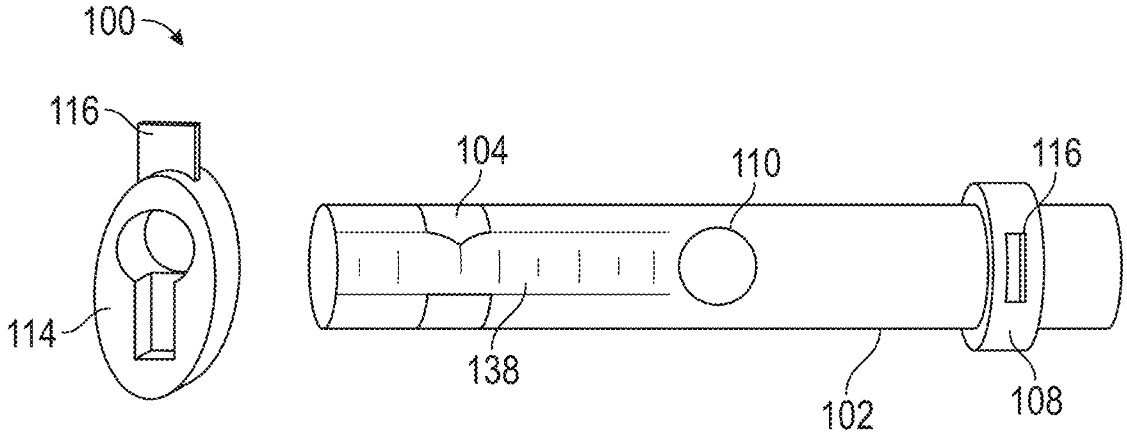
FIG. 2D illustrates the blade shield separate from the remainder of the exemplary ostomy bag preparation device, in accordance with some embodiments.

In some examples, the device 100 includes a blade shield 114 that removably covers at least the blade 106 of the cutting tool 104 to ensure user safety during measurement. Thus, as depicted by FIGS. 2C-2D, the method can include removing the blade shield 114. Preferably, the blade shield 114 may be removed after engaging the handle 110 to measure the stoma and before cutting the adhesive portion of the ostomy bag.

Figure 2E:
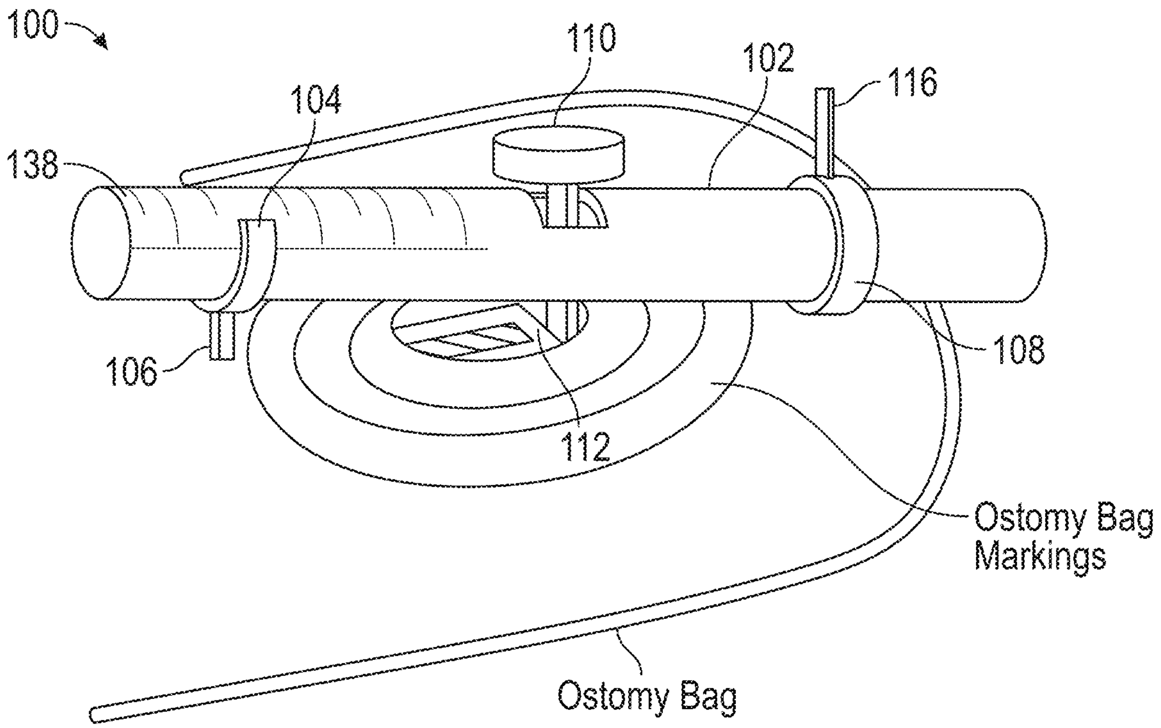
FIG. 2E illustrates inserting the cutting base of the exemplary ostomy bag preparation device into an opening of an ostomy bag, in accordance with some embodiments.

As shown in FIG. 2E, the method can include inserting the cutting base 112 of the device 100 into an opening of an ostomy bag to prevent cutting completely through the ostomy bag. The ostomy bag may be provided with a small opening (i.e., smaller than a stoma), and the cutting base 112 may be sized to be received in this opening. The cutting base 112 may pivot about the hinge 124 of the elongated housing 102 to be inserted into the opening in the ostomy bag.

Figure 2F:
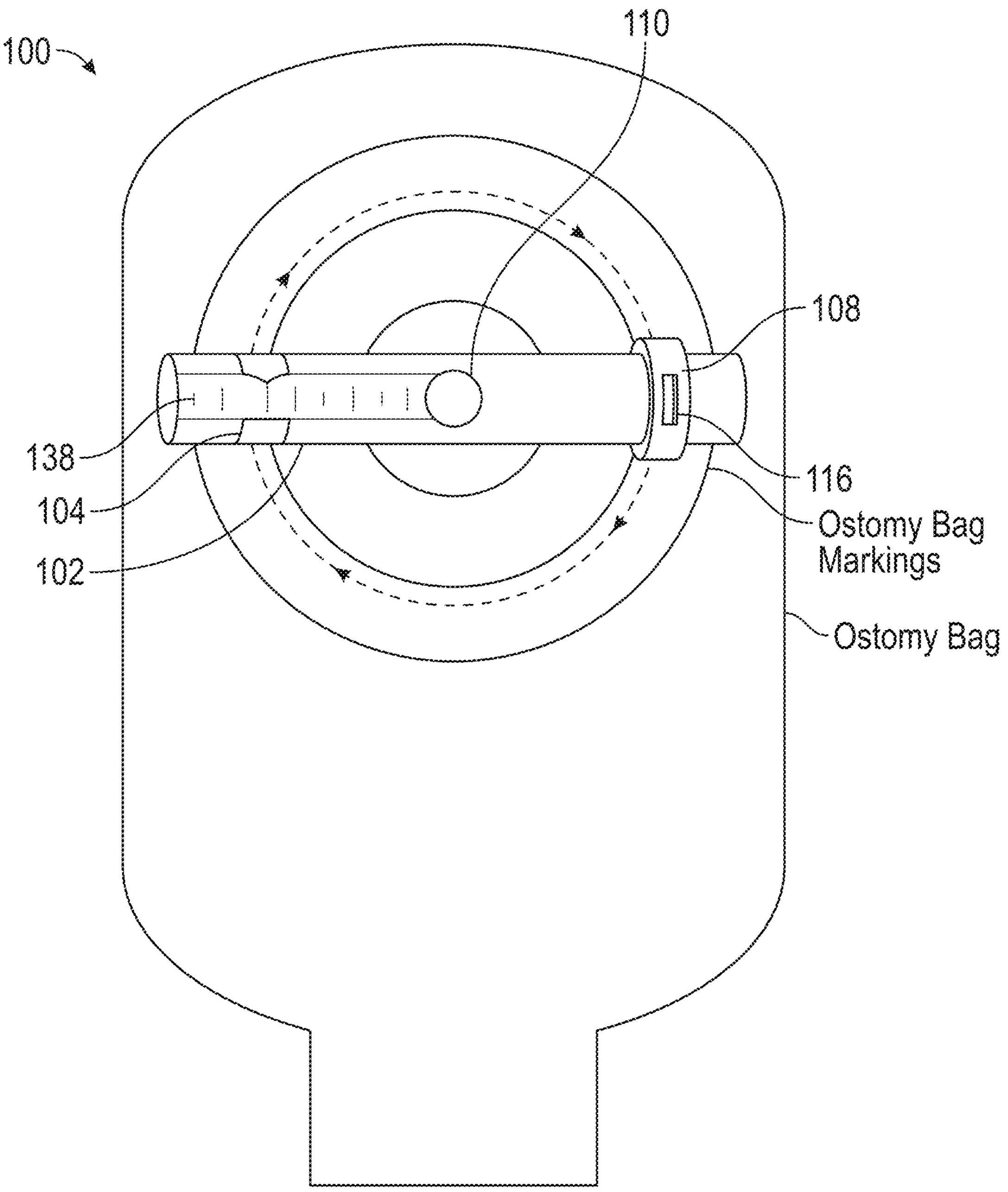
FIG. 2F illustrates rotating the elongated housing to cut through the adhesive portion of the ostomy bag using the blade of the cutting tool of the exemplary ostomy bag preparation device, in accordance with some embodiments.

As shown in FIG. 2F, once the cutting base 112 is properly inserted into the ostomy bag, the method can include rotating the elongated housing 102 (and the cutting base 112 attached thereto) to cut through an adhesive portion of the ostomy bag using the blade 106 of the cutting tool 104. The elongated housing 102 can be rotated 360° to completely cut a circumference of a hole in the ostomy bag that is appropriately sized for the subject's stoma. The circumference along which the ostomy bag is cut using the device 100 may not necessarily correspond to the markings depicted on the ostomy bag, but rather can correspond to the exact size necessary for a given subject's stoma. Accordingly, using the methods and devices provided herein, the stoma of a patient can be accurately sized, and the ostomy bag configured to adhesively attach to the stoma can be efficiently cut to correspond to this size.

Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

The numerical ranges disclosed inherently support any range or value within the disclosed numerical ranges, including the endpoints, even though a precise range limitation is not stated verbatim in the specification because this disclosure can be practiced throughout the disclosed numerical ranges.

CONCLUSION

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

What is claimed is:

1. A device for preparation of an ostomy bag system, comprising:

an elongated housing comprising at least one groove that extends at least a portion of a length of the elongated housing;

a cutting tool comprising a blade, the cutting tool at least partially surrounding a first portion of the elongated housing, wherein the at least one groove of the elongated housing is configured to receive the cutting tool to guide translation of the cutting tool along the elongated housing;

a measurement guide configured to measure a diameter of a stoma of a subject, the measurement guide at least partially surrounding a second portion of the elongated housing, wherein the at least one groove of the elongated housing is configured to receive the measurement guide to guide translation of the measurement guide along the elongated housing;

a handle comprising a pinion inserted to an opening of the elongated housing, the handle operably coupled to the cutting tool by a first rack and to the measurement guide by a second rack, the first rack and the second rack disposed within the elongated housing, and wherein engaging the handle causes each of the cutting tool and the measurement guide to translate along the elongated housing; and a cutting base coupled to the elongated housing at an end of the cutting base, the cutting base insertable to an opening of an ostomy bag and comprising a first planar surface configured to receive the blade of the cutting tool during cutting of an adhesive portion of the ostomy bag and a second planar surface opposite the first planar surface.

2. The device of claim 1, comprising a blade shield configured to removably cover at least the blade of the cutting tool.

3. The device of claim 2, wherein the blade shield comprises a marker that protrudes from an external surface of the blade shield to indicate the diameter of the stoma and a corresponding cutting diameter for the ostomy bag.

4. The device of claim 1, wherein the measurement guide comprises a marker that protrudes from an external surface of the measurement guide to indicate the diameter of the stoma and a corresponding cutting diameter for the ostomy bag.

5. The device of claim 1, wherein the elongated housing comprises measurement markings to measure the diameter of the stoma.

6. The device of claim 1, wherein engaging the handle causes (a) the measurement guide to translate along the elongated housing in a first direction, and (b) the cutting tool to translate along the elongated housing in a second direction, the second direction opposite the first direction.

7. The device of claim 1, wherein the measurement guide and the cutting tool are configured to translate along the elongated housing equidistantly.

8. The device of claim 1, wherein the handle comprises a knob, such that engaging the handle comprises rotating the knob to cause the measurement guide and the cutting tool to translate along the elongated housing.

9. The device of claim 1, wherein the blade of the cutting tool extends outward from a ring portion of the cutting tool toward the cutting base coupled to the elongated housing.

10. The device of claim 1, wherein the elongated housing comprises a hinge at a central region of the elongated housing that couples the end of the cutting base to the elongated housing, the cutting base configured to pivot about the hinge of the elongated housing.

11. The device of claim 1, wherein the elongated housing comprises:

a first housing portion;

a second housing portion; and a connector surrounding at least a portion of each of the first housing portion and the second housing portion to connect the first housing portion and the second housing portion, wherein the first housing portion and the second housing portion enclose the first rack, the second rack, and the pinion of the handle.

12. The device of claim 1, wherein a length of the elongated housing is between 50-150 mm.

13. The device of claim 1, wherein a length of the cutting base is at least 50% of the length of the elongated housing.

14. A method for preparing an ostomy bag system, comprising:

aligning an elongated housing of a device with a diameter of a stoma of a subject, the elongated housing comprising at least one groove that extends at least a portion of a length of the elongated housing, and the device comprising:

a cutting tool comprising a blade, the cutting tool at least partially surrounding a first portion of the elongated housing, wherein the at least one groove of the elongated housing is configured to receive the cutting tool to guide translation of the cutting tool along the elongated housing;

a measurement guide at least partially surrounding a second portion of the elongated housing, wherein the at least one groove of the elongated housing is configured to receive the measurement guide to guide translation of the measurement guide along the elongated housing;

a handle comprising a pinion inserted to an opening of the elongated housing, the handle operably coupled to the cutting tool by a first rack and to the measurement guide by a second rack, the first rack and the second rack disposed within the elongated housing; and a cutting base coupled to the elongated housing at an end of the cutting base, the cutting base comprising a first planar surface and a second planar surface opposite the first planar surface;

engaging the handle to cause the cutting tool and the measurement guide to translate along the elongated housing such that each of the measurement guide and the cutting tool align with the diameter of the stoma;

inserting the cutting base into an opening of an ostomy bag; and while the first planar surface of the cutting place receives the blade of the cutting tool, rotating the elongated housing to cut through an adhesive portion of the ostomy bag using the blade of the cutting tool.

15. The method of claim 14, wherein the device comprises a blade shield removably covering at least the blade of the cutting tool, and the method comprises removing the blade shield after engaging the handle to measure the stoma and before rotating the elongated housing to cut the adhesive portion of the ostomy bag.

16. The method of claim 14, wherein engaging the handle causes (a) the measurement guide to translate along the elongated housing in a first direction, and (b) the cutting tool to translate along the elongated housing in a second direction, the second direction opposite the first direction.

17. The method of claim 14, wherein the measurement guide and the cutting tool translate along the elongated housing equidistantly.

18. The method of claim 14, wherein the handle comprises a knob, such that engaging the handle comprises rotating the knob to cause the measurement guide and the cutting tool to translate along the elongated housing.

19. The method of claim 14, wherein the elongated housing comprises a hinge at a central region of the elongated housing that couples the end of the cutting base to the elongated housing, such that inserting the cutting base into the opening of the ostomy bag comprises pivoting the cutting base about the hinge of the elongated housing.

* * * * *